(12) United States Patent
Hamer

(10) Patent No.: US 9,415,926 B2
(45) Date of Patent: Aug. 16, 2016

(54) UNIVERSAL DISPENSER FOR SAFETY PROTECTION DEVICES, PACKAGING FOR USE THEREWITH, AND METHOD OF DISPENSING

(75) Inventor: Jeffery Lee Hamer, Springville, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 1623 days.

(21) Appl. No.: 12/178,757

(22) Filed: Jul. 24, 2008

(65) Prior Publication Data

US 2010/0018987 A1    Jan. 28, 2010

(51) Int. Cl.
*B65D 83/00* (2006.01)
*B65D 83/04* (2006.01)
*B65H 37/00* (2006.01)

(52) U.S. Cl.
CPC ........ *B65D 83/0454* (2013.01); *B65D 83/0472* (2013.01); *B65H 37/002* (2013.01); *B65H 2701/1942* (2013.01)

(58) Field of Classification Search
USPC ............ 221/1, 25, 26, 33, 34, 36, 41–43, 45, 221/46, 69–75, 92, 103, 119, 197, 208, 259, 221/277, 303, 311
See application file for complete search history.

(56) References Cited

U.S. PATENT DOCUMENTS

| | | | | |
|---|---|---|---|---|
| 2,303,346 A * | 12/1942 | Flood | ............................ | 156/152 |
| 2,465,876 A | 3/1949 | Hornung | | |
| 2,765,205 A * | 10/1956 | Capella et al. | ................. | 312/91 |
| 2,791,324 A * | 5/1957 | Knoop et al. | ................. | 206/568 |
| 3,301,395 A * | 1/1967 | Swezey | ......................... | 206/463 |
| 3,409,721 A * | 11/1968 | Applezweig | ................... | 514/170 |
| 3,410,450 A * | 11/1968 | Fortenberry | ...................... | 221/7 |
| 3,689,458 A * | 9/1972 | Hellstrom | ......................... | 6/530 |
| 3,729,892 A * | 5/1973 | Aslund et al. | ................... | 53/399 |
| 3,885,070 A * | 5/1975 | Chapman | ..................... | 428/42.3 |
| 4,648,930 A * | 3/1987 | La Mers | ....................... | 156/247 |
| 5,065,894 A * | 11/1991 | Garland | ......................... | 221/25 |
| 5,511,665 A * | 4/1996 | Dressel et al. | ................ | 206/532 |
| 5,788,284 A * | 8/1998 | Hirst | ............................. | 283/81 |
| 5,957,358 A | 9/1999 | Getz | | |
| 6,003,722 A | 12/1999 | Thurner | | |
| 6,425,888 B1 * | 7/2002 | Embleton et al. | ............. | 604/290 |
| D478,810 S * | 8/2003 | Wilson | ........................... | D9/732 |
| 6,604,653 B2 | 8/2003 | Millar | | |
| 6,915,907 B2 | 7/2005 | Myers | | |

(Continued)

FOREIGN PATENT DOCUMENTS

| | | |
|---|---|---|
| KR | 20-1997-0003623 | 4/1997 |
| KR | 20-0177668 | 4/2000 |
| KR | 20-0432992 | 12/2006 |

OTHER PUBLICATIONS

International Search Report from PCT/US2009/051106 dated Feb. 25, 2010.

*Primary Examiner* — Gene Crawford
*Assistant Examiner* — Kelvin L Randall, Jr.

(57) ABSTRACT

A dispenser arrangement including an elongated strip of packaged safety protection devices disposed at an interior of the dispenser, a drive arrangement configured to advance and rupture the strip of packaged safety protection devices and to release the safety protection devices therefrom at the demand of a user, a waste arrangement configured to receive and retain the strip of packaging after release of the safety protection devices.

28 Claims, 12 Drawing Sheets

(56) References Cited

U.S. PATENT DOCUMENTS

| | | |
|---|---|---|
| 6,962,266 B2 | 11/2005 | Morgan |
| 7,857,135 B2 * | 12/2010 | Martin et al. ............. 206/542 |
| 2004/0065670 A1 | 4/2004 | Morgan |
| 2004/0079579 A1 * | 4/2004 | Barwacz .................. 181/135 |
| 2005/0154491 A1 | 7/2005 | Anderson |
| 2008/0173317 A1 * | 7/2008 | Robinson et al. ......... 131/112 |

\* cited by examiner

UNIVERSAL DISPENSER FOR SAFETY PROTECTION DEVICES, PACKAGING FOR USE THEREWITH, AND METHOD OF DISPENSING

TECHNICAL FIELD OF INVENTION

The invention generally concerns a mechanism for storing and dispensing consumer products. More particularly, the invention concerns a dispenser mechanism for storing and allowing access to prepackaged safety protection devices as well as a method for dispensing such devices and a packaging used therewith.

BACKGROUND OF INVENTION

Safety protection devices, such as earplugs, are routinely used in consumer, commercial, and industrial environments. Often, earplugs are distributed in large volumes to a substantial number of users. For example, in a factory or manufacturing setting, earplugs may be provided to all workers and visitors in compliance with safety regulations.

Common modes of earplug distribution include box distribution and mechanical dispenser distribution. One form of box distribution consists simply of a box containing numerous earplugs placed in an open condition in an accessible area. This would include, for example, a box of one-hundred earplugs (individual earplugs or corded pairs, packaged or unpackaged) placed on a table in a work room with the box top open for access by workers. Another, more sophisticated box distribution may be found in U.S. Pat. No. 6,915,907 in the name of Brian Myers which granted on Jul. 12, 2005 and which is hereby incorporated by reference in its entirety. This reference discloses distribution of multiple types of packaged earplug pairs through a plurality of lower access ports.

These earplug box distribution arrangements may be convenient, simple, and inexpensive. However, in the case of box distribution of unpackaged earplugs, a sanitary condition of the earplugs cannot be guaranteed after multiple user access attempts. Also, the number of earplugs distributed per user cannot be regulated. That is, a user who only needs two earplugs, may inadvertently remove three or four unpackaged earplugs from the box and then discard unnecessary plugs, thus leading to product waste. In the case of box distribution of packaged earplugs, the box arrangements do not make provision for collection, disposal, or recycling of the packaging. Thus, when a packaged earplug pair is accessed from the box, the earplugs are removed from the package and then often the package is not properly disposed or recycled (e.g., the package is left on a table, dropped on a floor, or placed in a rubbish bin instead a plastic recycling receptacle). The result is an untidy dispensing area littered with spent packaging which is not properly collected for recycling. Additionally, with this mode of distribution, the quantity of earplug packages accessed by a user is not controlled. Thus, as with non-packaged earplugs, here the user may access a handful of packaged earplug pairs when only one package is needed; additional packages may be discarded thus further wasting product.

Mechanical earplug dispensers typically consist of a hopper which contains loose, non-packaged earplugs, and a mechanical arrangement designed to release earplugs upon demand of a user. Such a dispenser is disclosed, for example, in U.S. Pat. No. 6,604,653 in the name of Timothy Millar which granted on Aug. 12, 2003 and which is herein incorporated by reference in its entirety. These type of dispensers provide a convenient means for accessing earplugs and can maintain the non-packaged earplugs in a sanitary condition prior to user access but they can be relatively expensive, require frequent refill, and, depending on the particular dispenser, can be prone to malfunction by jamming of the earplugs within the mechanical distribution arrangement. Moreover, these type of dispensers are typically configured to only distribute regularly shaped, non-stemmed, non-corded earplugs such as cylindrical foam earplugs. Conventional mechanical dispensers cannot handle earplugs with stems extending therefrom, nor corded earplug pairs, nor packaged earplugs, or irregularly shaped earplugs.

Other safety protection devices, beyond earplugs, include, for example, safety eyewear, respirators, ventilators, safety gloves, and various components and accessories of thereof. These safety protection devices are typically distributed on site by an open-box type arrangement as discussed above with respect to earplugs. For example, at a work site, a box containing a plurality of safety eyewear devices is simply placed at an easily accessible area, such as on a table, and the box top is placed into an open position to expose the contents therein. Users simply reach in to the box to access the safety eyewear devices. This open-box distribution presents the same disadvantages previously described concerning the box distribution of earplugs. That is, sanitary conditions may not be maintained, there is no control of the quantity of items distributed, associated packaging is not collected for recycling, etc. Mechanical dispensers of these additional safety protection devices are simply not available.

Accordingly, there is a need for a universal dispenser mechanism which can store packaged safety protection devices of any form, shape, and size (e.g., earplugs that are corded, stemmed, etc., safety eyewear, etc.), which can readily and easily dispense such devices in an unpackaged condition upon demand by a user, and which dispenser mechanism includes waste and recycling provisions for the empty packaging, where the safety protection devices are maintained in a sanitary condition prior to dispensement and where the quantity of dispensed devices is controlled.

BRIEF SUMMARY OF THE INVENTION

The above discussed and other problems and deficiencies of the prior art are overcome or alleviated by the invention which provides a novel and nonobvious dispenser for safety protection devices.

A dispenser arrangement is provided including an elongated strip of packaged safety protection devices, such as hearing protection devices, disposed at an interior of the dispenser, a drive arrangement configured to advance and rupture the strip of packaged hearing protection devices and to release the hearing protection devices therefrom upon demand of a user, and a waste arrangement configured to receive and retain the strip of packaging after said release of the hearing protection devices.

In another embodiment, a product dispenser arrangement is disclosed including a spool configured to releasably retain a wound package including a plurality of the products, a drive mechanism activatable by a user and configured to advance the wound package and to release individual products therefrom for deposit with the user, a waste mechanism configured to receive and retain the package after release of said individual products.

Also provided is a method of dispensing safety protection devices, such as hearing protection devices, where the method includes disposing said hearing protection devices at intervals along an elongated package strip, perforating the package strip along a length thereof, storing the package strip within a dispenser, advancing the package strip from the storage, rupturing the package strip along the perforation to release the intervally disposed hearing protection devices, and collecting the package strip for disposal after said releasing of the hearing protection devices.

The above-discussed and other features and advantages of the apparatus and method of the invention will be appreciated and understood by those skilled in the art from the following drawings and detailed description.

BRIEF DESCRIPTION OF THE FIGURES

Referring now to the drawings wherein like elements are numbered alike in the several FIGURES.

DETAILED DESCRIPTION OF THE INVENTION

Figure 1:
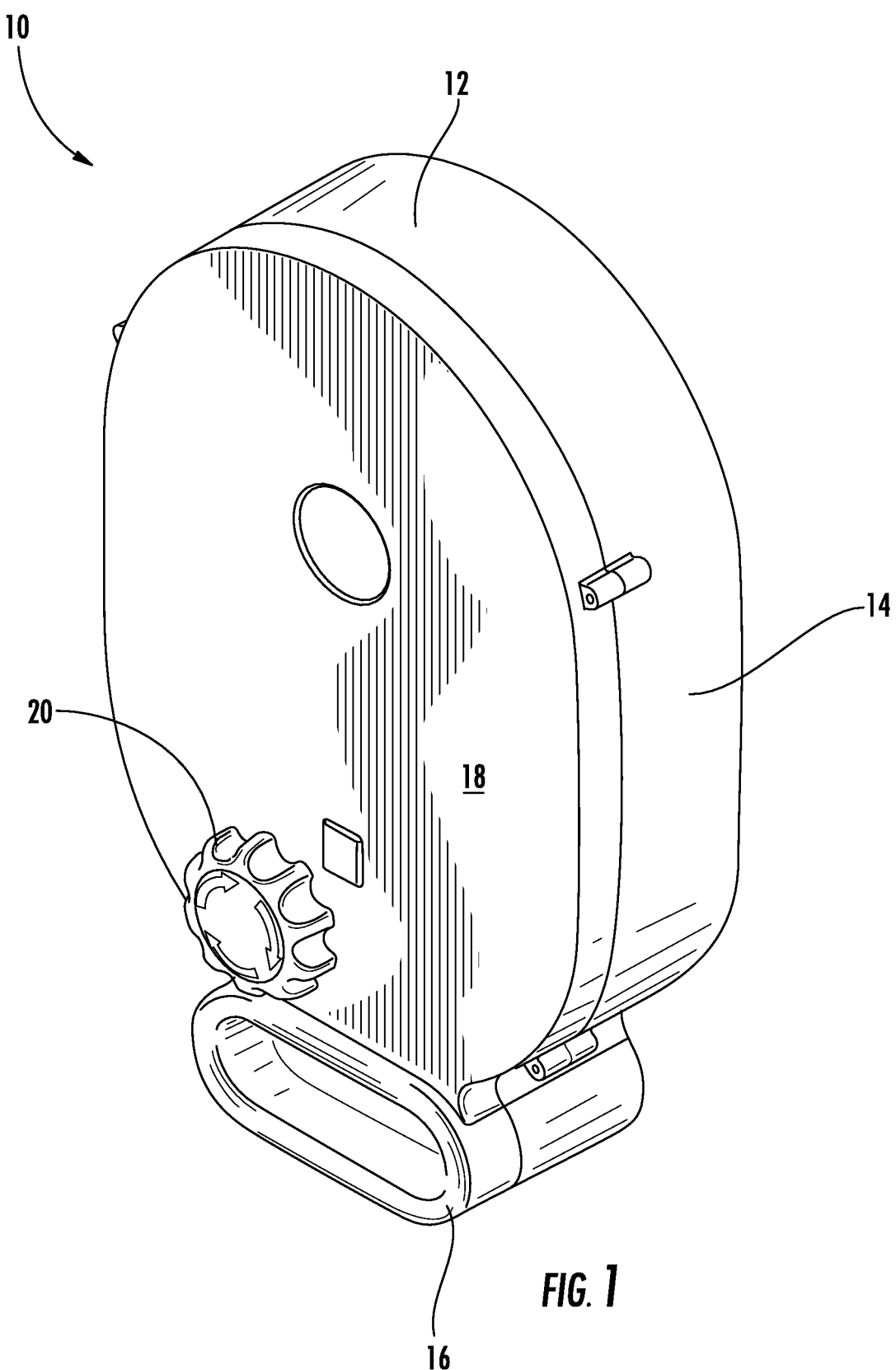
FIG. 1 is a perspective view of a dispenser.

FIG. 1 shows a dispenser 10 in an exemplary embodiment of the invention. The dispenser 10 includes a body 12 having a storage portion 14 and a dispensing portion 16. The storage portion 14, as will be further discussed, is essentially a housing which contains packaged safety protection devices and a mechanical assembly which unpackages the safety protection devices, distributes them to a user, and then stores the spent packages. The dispensing portion 16 is a receptacle where the dispensed safety protection devices are presented to the user. In this embodiment, the dispensing portion 16 is an oval shaped cavity disposed at a lower potion of the body 12 which has an open front through which the dispensed devices may be accessed by the user.

Figure 2:
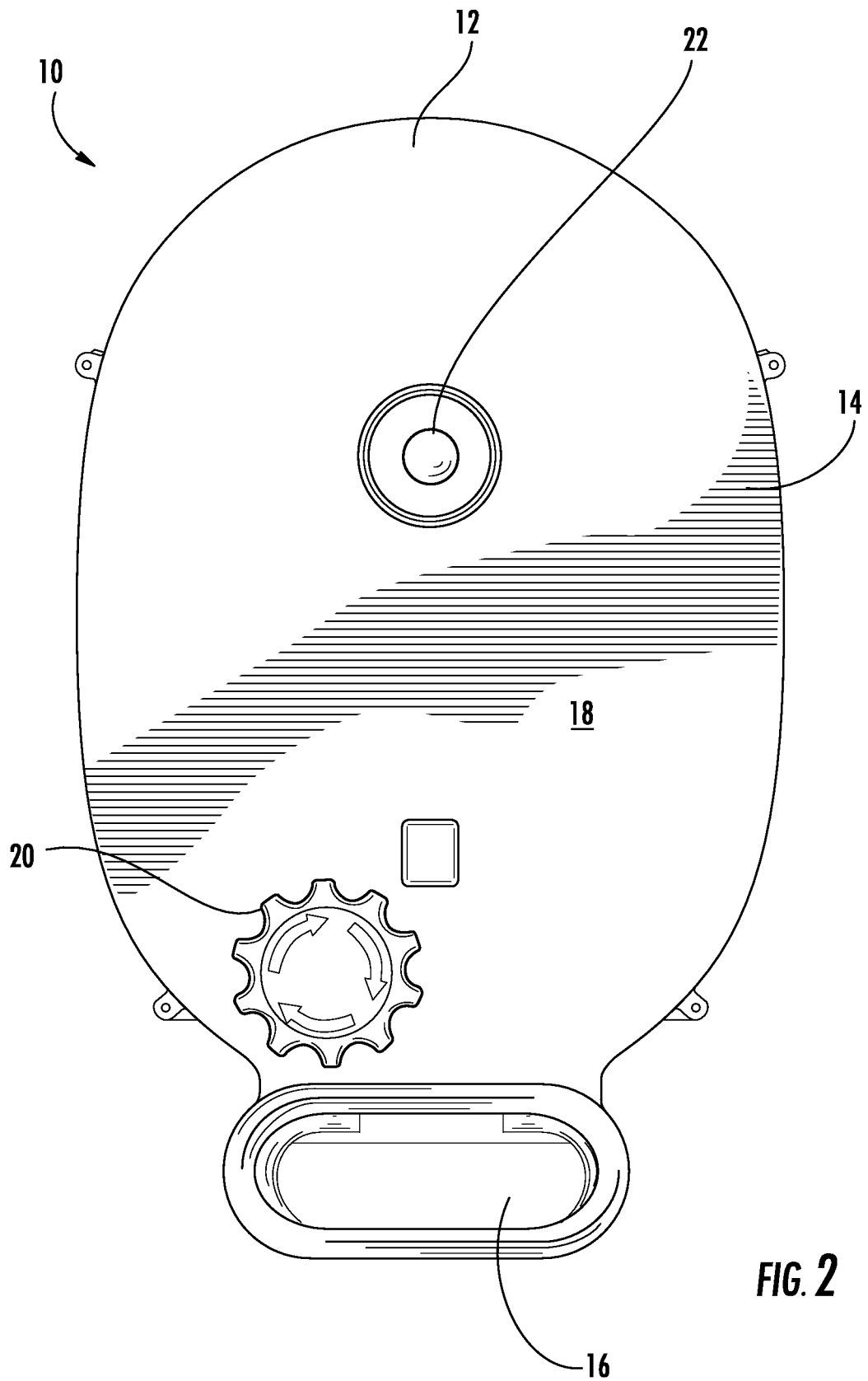
FIG. 2 is a front elevation view thereof.
Figure 3:
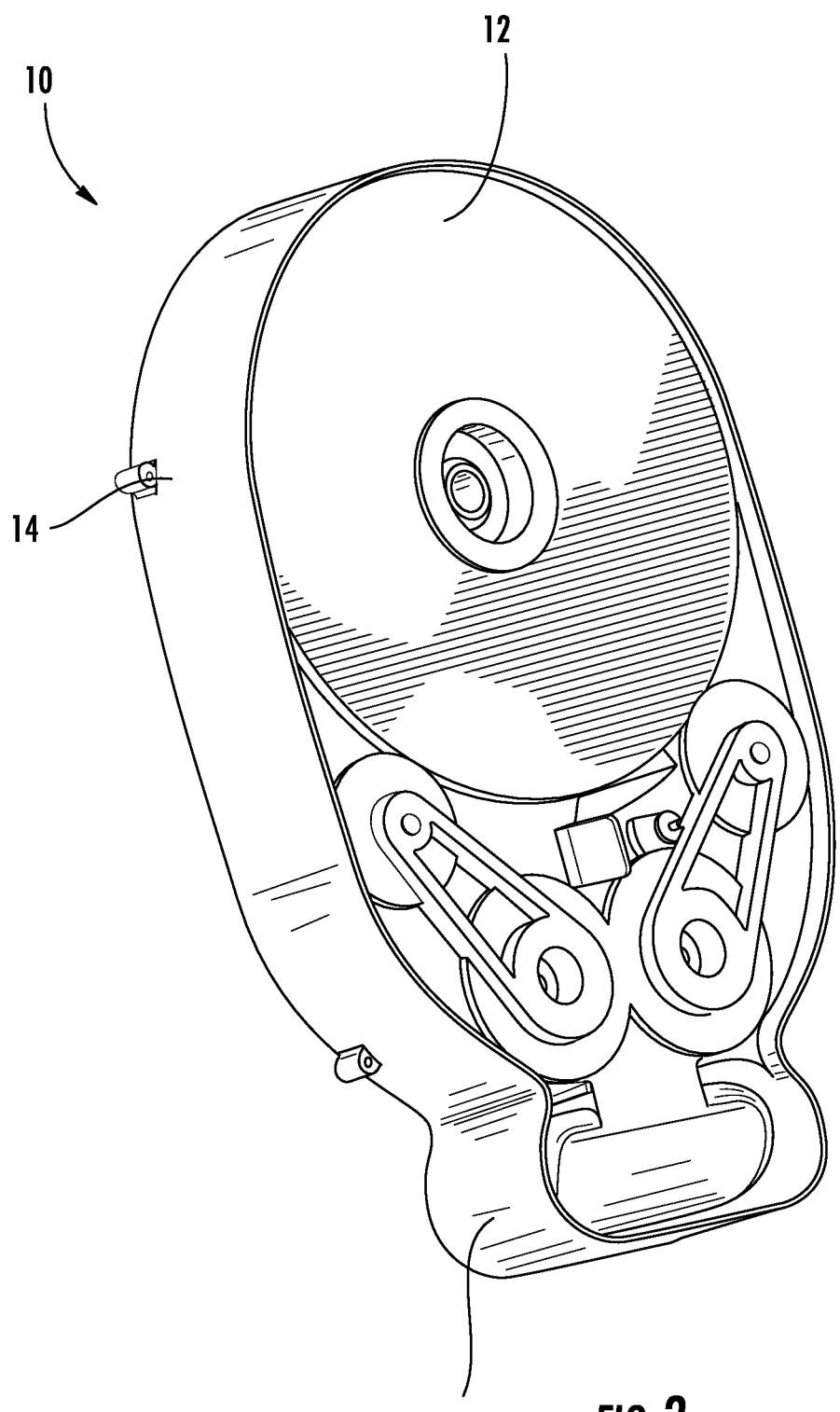
FIG. 3 is a rear perspective view thereof.
Figure 4:
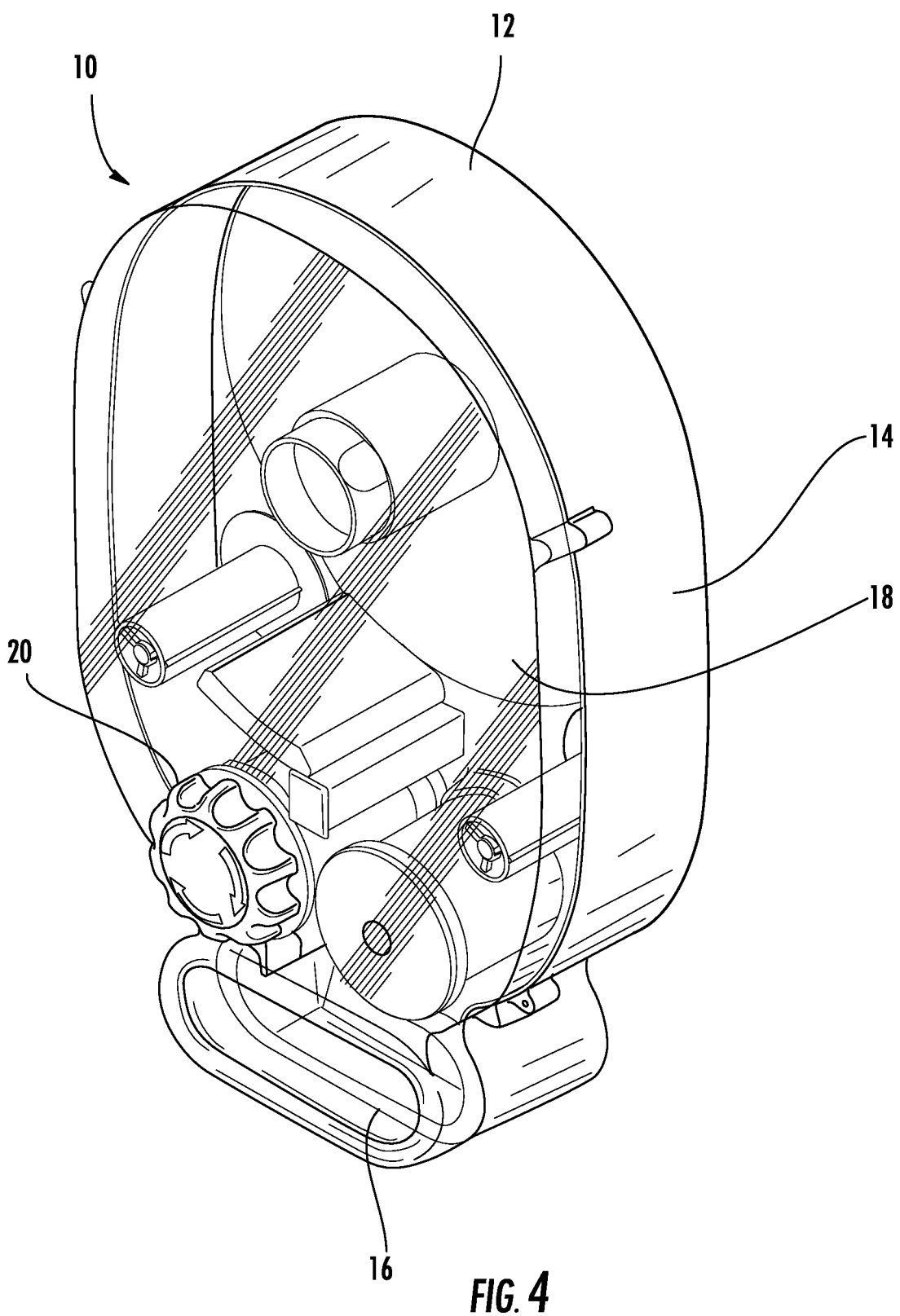
FIG. 4 is a front perspective view thereof with a transparent cover.

The body 12 further includes a removable front cover 18. The cover 18 can be an opaque member as shown in FIGS. 1 and 2 or it may be transparent as shown in FIG. 4. The cover 18 is removably fixed to the body 12 by any sufficient fixating arrangement including screws, clasps, clips, etc. An actuator 20 is disposed on the cover 18 and includes gearing which extends through cover 18 and interacts with the mechanical assembly within the dispenser 10. Here, the actuator 20 is presented as a rotatable knob. In other embodiments, the actuator 20 may comprise a lever, push-button, switch, etc. This actuator may be a manually driven device or an electronically operated arrangement.

Figure 5:
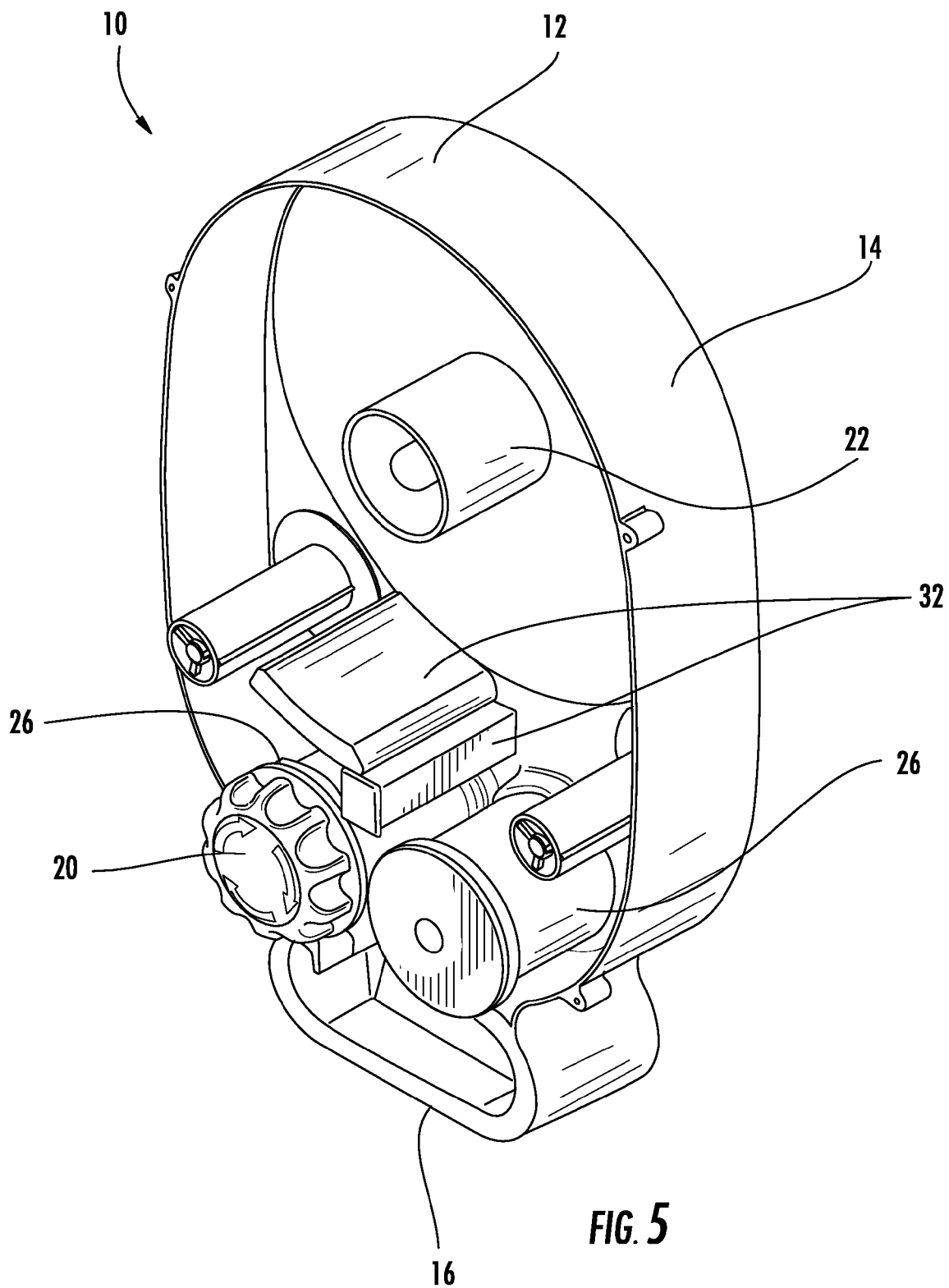
FIG. 5 is a front perspective view thereof with the cover removed.
Figure 6:
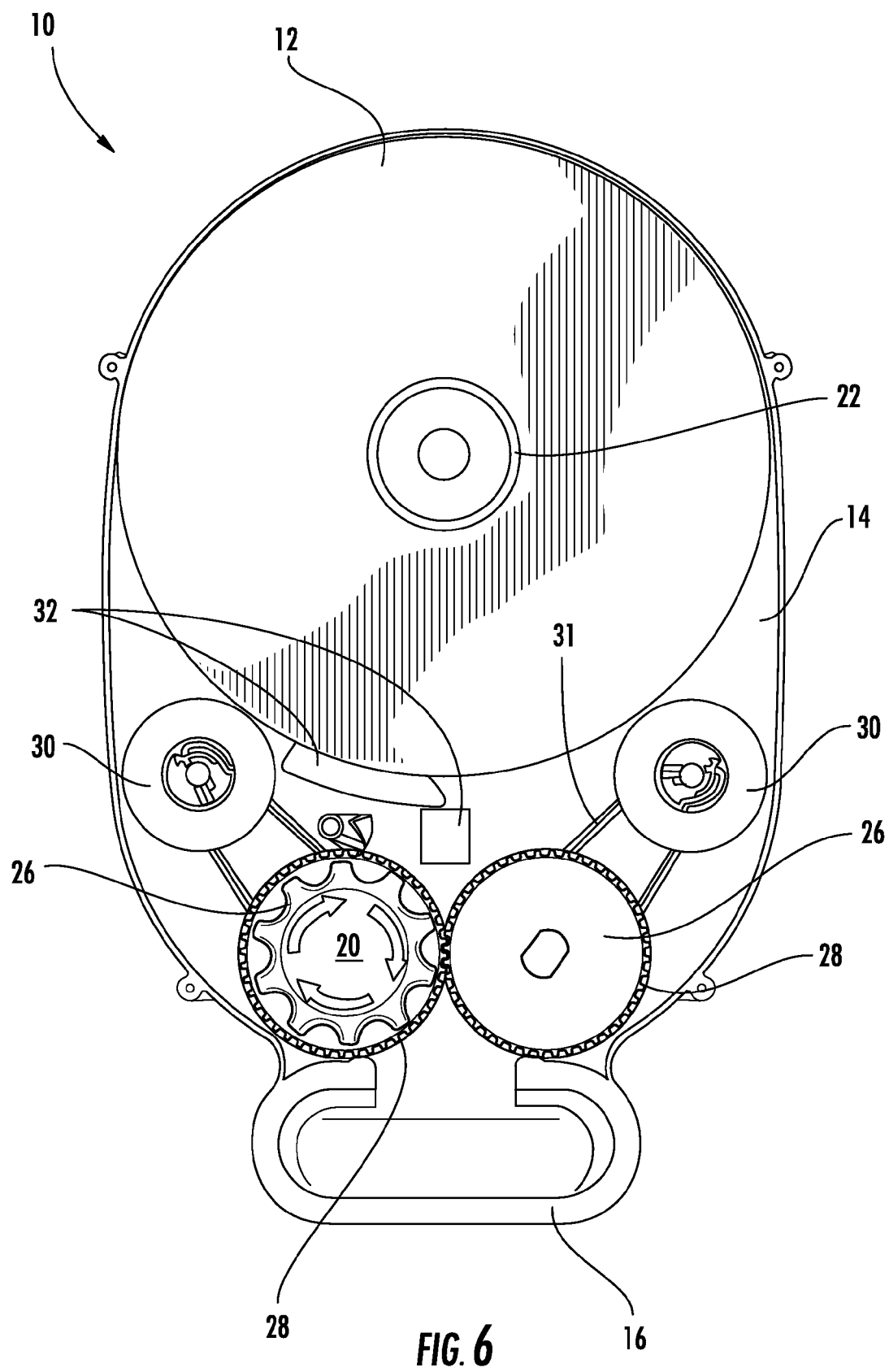
FIG. 6 is a front elevation view thereof.
Figure 7A:
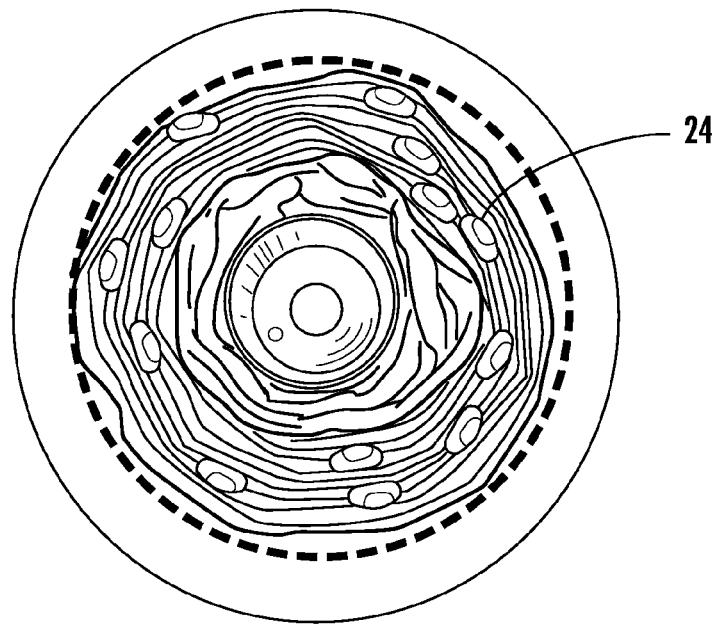
FIGS. 7A-7C are various views of a strip of packaged safety protection devices.
Figure 7B:
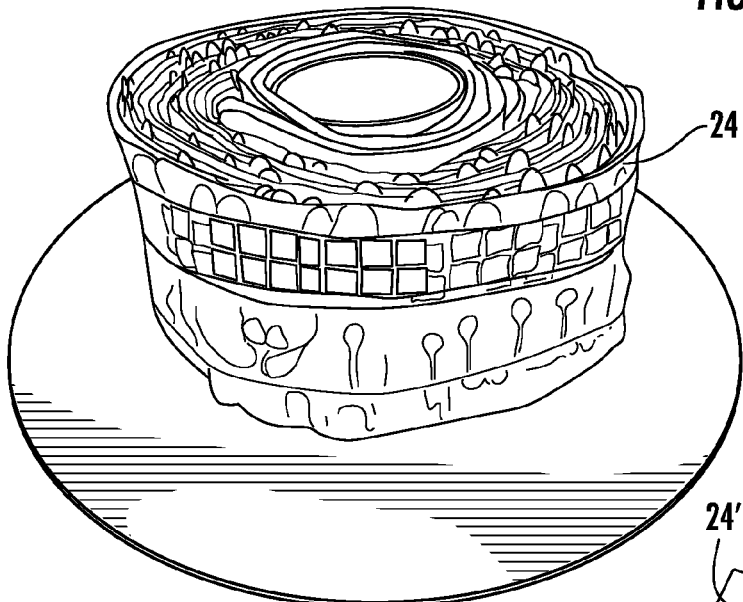
Figure 7C:
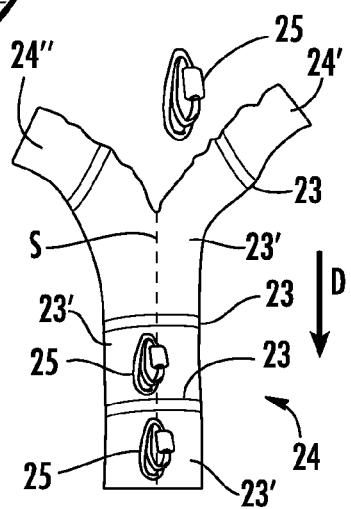

FIGS. 5 and 6 illustrate the dispenser 10 with the cover 18 removed, thus showing the interior of the dispenser 10. Therein, the dispenser 10 includes a main spool 22 which is configured to receive and retain a spooled configuration of packaged safety protection devices 24 (see, FIGS. 7A and 7B). In this exemplary embodiment, the safety protection devices 24 are packaged hearing protection devices 24 which comprise a strip of earplug pairs 25, each pair individually packaged, each packaged pair being attached to a first and second adjacent packaged pair, thus forming an elongated packaging strip. In one embodiment, the package strip 24 comprises an essentially continuous package envelope, as shown in FIG. 7C. The package strip 24 includes sealing 23 across its width in various locations. The seal 23, for example, may be a weld line or the like. The sealing 23 is placed at intervals to form individual package pouches 23' which each pouch 23' includes an earplug pair 25. The package strip 24 may be composed of a plastic film or the like. Here, for purposes of illustration, the packaged earplug pairs 25 each comprise a pair of foam earplugs connected to each other with a cord. Of course any of a variety of hearing protection devices may be packaged as discussed and used in conjunction with the invention. Moreover, hearing protection devices are discussed herein merely as one exemplary type of safety protection device which may be used in conjunction with the invention. Other safety protection devices which may be incorporated with this invention include but are not limited to safety eyewear devices, head and face protection devices, respirator devices, fall protection devices, etc. Additionally, general consumer products may be utilized with the dispenser and method of dispensing as described herein.

Returning to the exemplary FIG. 7C, the strip of packaged hearing protection devices 24 further includes a perforation P, on its exterior which allows for ready tearing of the package and facilitates access to the earplug pair 25 disposed therein. Particularly, the package strip 24 includes a perforation P which extends along its length. The perforation P is essentially a series of centrally formed punctures in the strip 24 which extend longitudinally along the package strip 24. The perforation P allows the package strip 24 to be separated into two halves 24' and 24". This separation or rupture of the package strip 24 releases the earplug pairs 25 disposed therein. Due to the seals 23, only one earplug pair 25 can be released at a time as the strip 24 is separated along the perforation P in the direction D.

The dispenser 10 further includes rollers 26 disposed at the interior. In this embodiment, a pair of the rollers 26 are disposed adjacent to one another beneath the main spool 22 proximate to the dispensing portion 16. See, FIGS. 5-6. The actuator 20 is attached to at least one of the two rollers 26. Both rollers 26 are disposed rotatably on the body 12 of the dispenser 10. Specifically, each roller 26 is configured to rotate about its longitudinal axis. The rollers 26 each include gearing 28 which is intermeshed between the rollers 26. In this way, rotation of one of the rollers 26 correspondingly rotates the adjacent roller 26. The removable front cover 18 includes an opening through which the actuator 20 extends to an exterior of the dispenser 10. The externally exposed actuator 20 may be accessed and manipulated by a user. The actuator 20 is disposed in fixed relation to one of the rollers 26. Rotation of the actuator 20 rotates a first of the rollers 26. Rotation of the first roller 26 drives a corresponding rotation of the second roller 26 via the gearing 28.

The dispenser 10 further includes a pair of waste spools 30 disposed at the interior thereof The waste spools are disposed generally between the main spool 22 and the rollers 26. See, FIG. 6. As will be discussed in greater detail below, the waste spools 30 are configured to receive and releasably retain spent hearing protection packaging 24' and 24", i.e., the packaging 24 after the devices are removed therefrom. The spent packaging 24' and 24" is stored on the waste spools 30 until removed for disposal and recycling. The waste spools 30 are engaged with the rollers 26 such that rotation of the latter affects a corresponding rotation on the former.

The dispenser 10 further includes a plurality of guides 32 centrally disposed at the interior of the dispenser 10 and adjacent to the main spool 22. These guides 32 are configured to direct the hearing protection device packaging strip 24 toward the rollers 26 to facilitate engagement therewith. Additionally, the guides 32 are configured and arranged to center the earplug pair 25 within the respective individual package pouch 23'. This advantageously centrally positions the earplug pair 25 in order to facilitate prompt ejection of the earplug pair 25 from the individual packaging pouch 23' when the packaging strip 24 is separated along the perforation P, as further described herein.

Figures 8, 9:
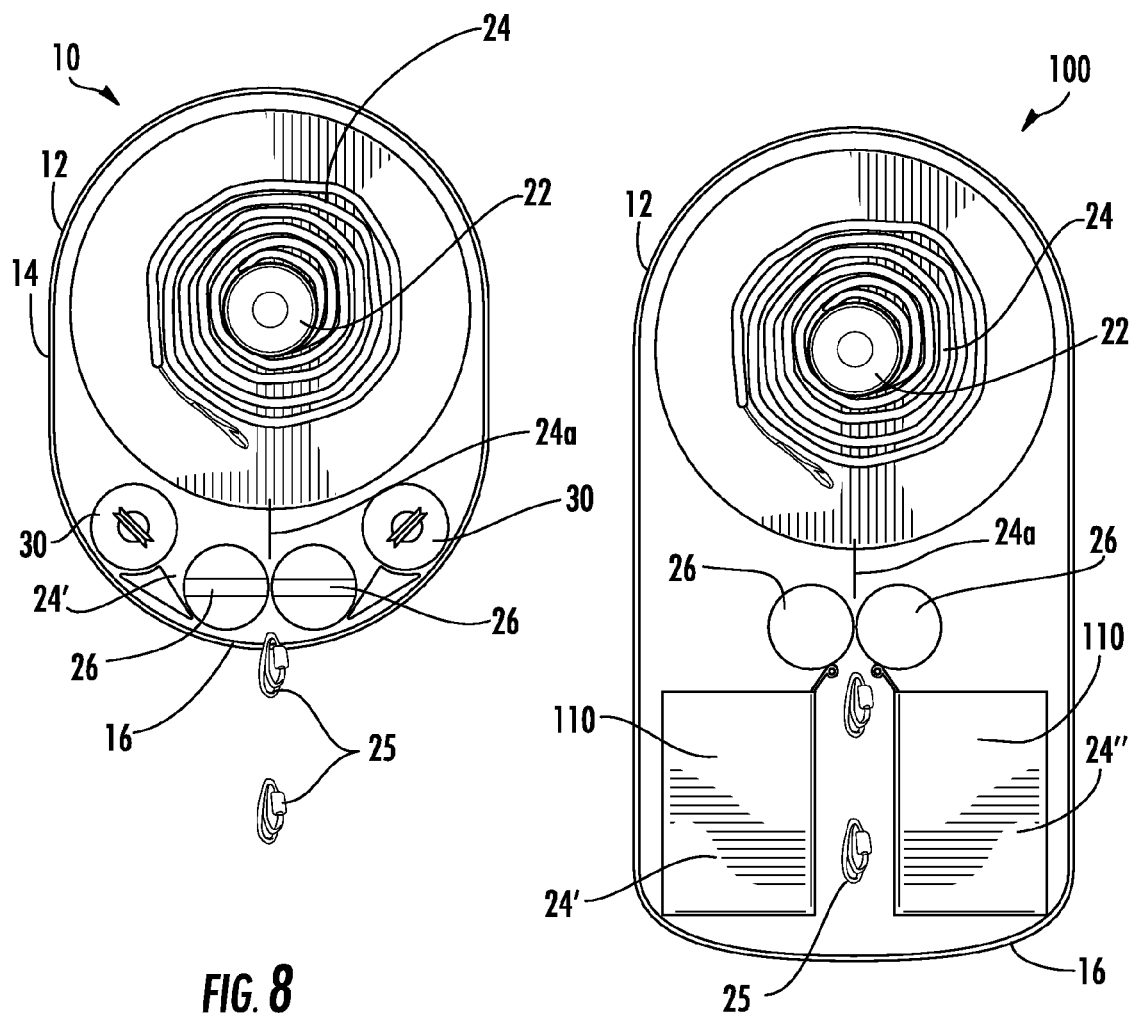
FIG. 8 is front view of the dispenser of FIG. 1.
FIG. 9 is a front view of the dispenser in another embodiment.

FIG. 8 shows the dispenser 10 in use. As illustrated, the dispenser 10 includes the spooled configuration of packaged hearing protection devices 24 disposed at the main spool 22. The strip of packaged hearing protection devices 24 is essentially wound around the main spool 22, for example, in a counter clockwise direction. A leading end 24a of the package strip 24 descends from the main spool 24, traverses the guides 32, and extends between the rollers 26. The package strip 24 is pressed between the rollers 26 such that a clockwise rotation of the actuator 20 causes a clockwise rotation of the proximate roller 26 and a corresponding counter clockwise rotation of the opposite roller 26 to thus pull the hearing protection device packaging strip 24 in a downward direction between the rollers 26 and away from the main spool 22. That is, rotation of the actuator 20 pulls the package strip 24 downward, thus unraveling the strip 24 from the main spool 22.

The leading end 24 of the packing strip includes portions 24' and 24" which are delimited by the perforation P and which diverge therefrom. These portions 24' and 24" are fed around and under the rollers 26 and are affixed to the waste spools 30. As the package strip 24 traverses the rollers 26, the strip 24 is separated or ruptured at the perforation P so as to open the individual packaging pouches 23' and free the hearing protection devices 25 therefrom. That is, a user rotates the actuator 20, for example, in a clockwise direction. This rotates the roller 26 which is connected to the actuator 20 in a corresponding clockwise direction. Due to the gearing described above, an opposite counter-clockwise rotation is imparted upon the other roller 26. The engagement of the rollers 26 and waste spools 30 translates the rotation of the former onto the latter. The result is a clockwise rotation of the waste spool 30 associated with the roller 26 which is attached to the actuator 20. A counterclockwise rotation is imparted upon the second waste spool 26 which is associated with the other, non-actuator, roller 26. The result is that the portions 24' and 24" are pulled in opposite directions. For example, the portion 24' passes on the underside of the roller 26 associated with the actuator 20 and then the portion 24' extends to a fixation with the corresponding waste spool 30 such that the portion 24' is spooled on the waste spool 30 in a clockwise direction as the dispenser is used. The other portion 24" of the packaging strip 24 passes under the non-actuator roller 26 and is spooled upon the corresponding waste spool 30 in a counterclockwise rotation. The spent portions 24' and 24" are conveniently stored at the waste spools 30 for later removal and recycling.

The hear protection devices 25 are liberated from the packaging 24 as the individual pouches 23' are ruptured by separation of the strip 24 at the perforation P. That is, as discussed, the guides 32 position the earplug pairs 25 centrally within the individual packaging pouches 23' as the packaging strip 24 traverses thereby. Each pouch 23' is ruptured at the perforation P in succession as the packaging strip 24 moves through the rollers 24. When a respective pouch 23' is split open, the earplug pair 25 contained therein falls from the packaging strip 24 downward into the dispensing portion 16 of the dispenser 10 where the user can then grasp the earplug pair 25. Centrally positioning the earplug pair 25 within the pouch 23' via the guides 32 advantageously removes the pair 25 from the corners of the pouch 23' (or from other undesirable areas within the pouch) where the earplug pair 25 could interfere with separation of the packaging strip 24 or get stuck within the packaging and thus fail to discharge.

As mentioned, the spent, empty packaging portions 24' and 24" are directed by the rollers 26 toward the waste spools 30. The spent packaging 24' and 24" is wound around these waste spools 30 and collected there until removed and discarded and/or recycled. The dispenser 10 may further include a recycling receptacle for receiving used safety protection devices. In this embodiment, the receptacle may comprise a hopper attached to or extending from the body 12 of the dispenser 12. The hopper would be configured to receive and retain the earplug pairs 25 deposited therein by users after the earplugs 25 have been worn. This recycling receptacle of course could take a different form or configuration depending upon the particular disposal/recycling requirements of the specific safety protection device at issue.

FIG. 9 illustrates an alternate embodiment of the invention. Therein, a dispenser 100 is shown as including many of the elements of the dispenser 10 described above. Similar parts of the various dispenser embodiments discussed herein are indicated with corresponding reference numerals throughout the Figures. For sake of brevity, these like parts are not re-introduced in detail, unless where otherwise noted. The dispenser 100 includes the hearing protection device package strip 24 wound around the main spool 22 with the leading edge 24a extending downward between the rollers 26. As described with regard to the dispenser 10, as the package strip 24 passes through the rollers 26, the package strip 24 is ruptured at the scoring to thus release the earplug pairs 25. The actuator 20 is used to manually rotate the rollers 26 of the dispenser 100, in similar manner to the dispenser 10. However, instead of the waste spools 30 of the dispenser 10, the current dispenser 100 includes waste bins 110 which receive the spent package strip portions 24', 24". The waste bins 110 are receptacles disposed within the body 12 of the dispenser 100 proximate to the dispensing portion 16. The bins 110 are arranged to collect the spent package material 24' and 24" as the earplug pairs 25 are released therefrom. In one example, the bins 110 are configured to receive the spent package 24' and 24" and fold the package 24' and 24" in a "z" type arrangement. That is, as the spent packaging 24' and 24" enters the waste bins 110, it folds back and forth upon itself in a "z" shaped pattern. The spent packaging 24' is deposited in one of the waste bins 110 while the other portion of the spent packaging 24" is directed to the opposite waste bin 110. The waste bins 110 may be accessed by removing the cover 18 from the dispenser 100. The user then may reach into the bins 110 empty the spent packaging 24' and 24" and proceed to recycle the spent packaging. Alternatively, the waste bins 110 may be configured to be removable from the dispenser 100. Thus, the cover 18 may be removed and then the bins 110 may each be removed, emptied, and then reinserted.

The dispenser 100 is operated by a user similarly to the dispenser 10. That is, the user simply rotates the actuator 20 which thus rotates the rollers 26 and pulls the package strip 24 downward into the rollers 26. As the strip 24 engages the rollers 26, the strip 24 is ruptured and the earplugs 25 disposed therein are released and dropped into the dispensing portion 16 where the user may grasp and remove the earplug pair 25. The dispenser 100 may include the guides 32 described above for positioning the earplug pairs 25 centrally with the respective packaging pouch 24 prior to discharge thereof Further, the dispenser 100 may include a recycling receptacle, as discussed above, for receiving and storing used earplug pairs 25. Of course, the earplug pairs 25 are discussed herein only by way of example and the dispenser 100 may be alternatively used to distribute other types of safety protection devices an/or other consumer oriented products.

FIGS. 10-17 show dispensers in additional embodiments of the invention.

Figure 10:
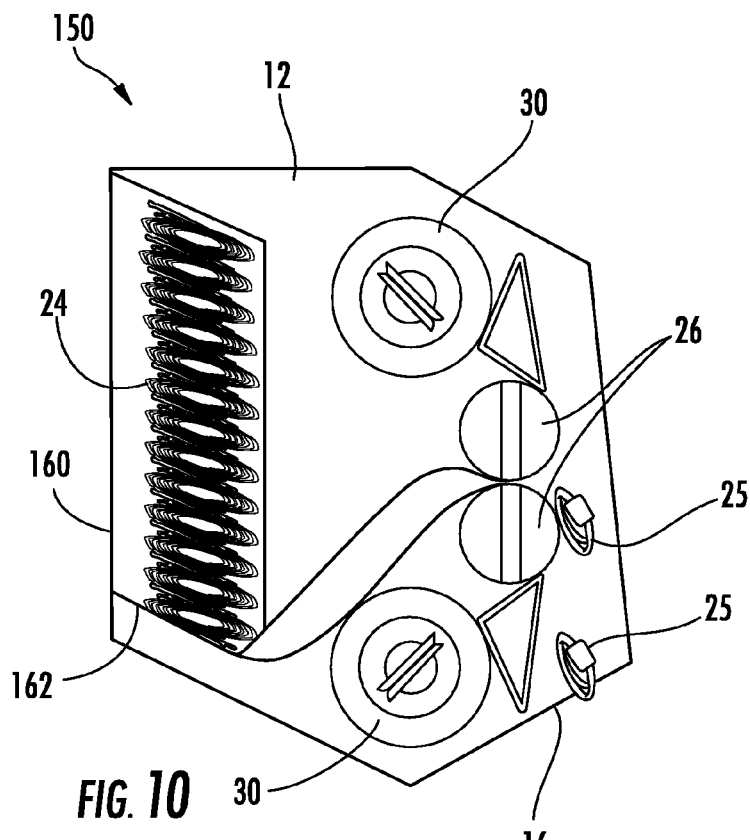
FIGS. 10 and 11 are front views of the dispenser in another embodiment.

FIG. 10 illustrates a dispenser 150 which includes the rollers 26 and the waste spools 30 discussed above concerning dispensers 10 and 100. But here, the dispenser 150 includes the hearing protection device package strip 24 folded in a "z" configuration and disposed within a cartridge 160 at the interior of the dispenser 150. That is, the package strip 24 is folded back and forth upon itself within the cartridge 160. The leading edge 24a of the package strip 24 exits the cartridge at a slanted base 162 thereof The leading edge 24a extends to and between the rollers 26 as illustrated. The slanted base 162 is a lower portion of the cartridge 160 which descends at a slight angle relative to a horizontal. This naturally disposes the "z" folded package strip 24 at a corresponding angle within the cartridge 160 and can facilitate egress of the strip 24 from the cartridge 160.

In use, a user manually rotates an actuator (not shown) to draw the package strip 24 between and through the rollers 26. As described, this action separates the strip 24 along the perforation P and liberates the corded earplug pair 25 disposed therein. The earplugs 25 fall from the package strip through the dispensing portion 16 into the waiting hand of the user or into some type of catch device. The spent packaging 24' and 24" is wound around the waste spools 30 as discussed regarding the dispenser 10 and is stored for later recycling.

Figure 11:
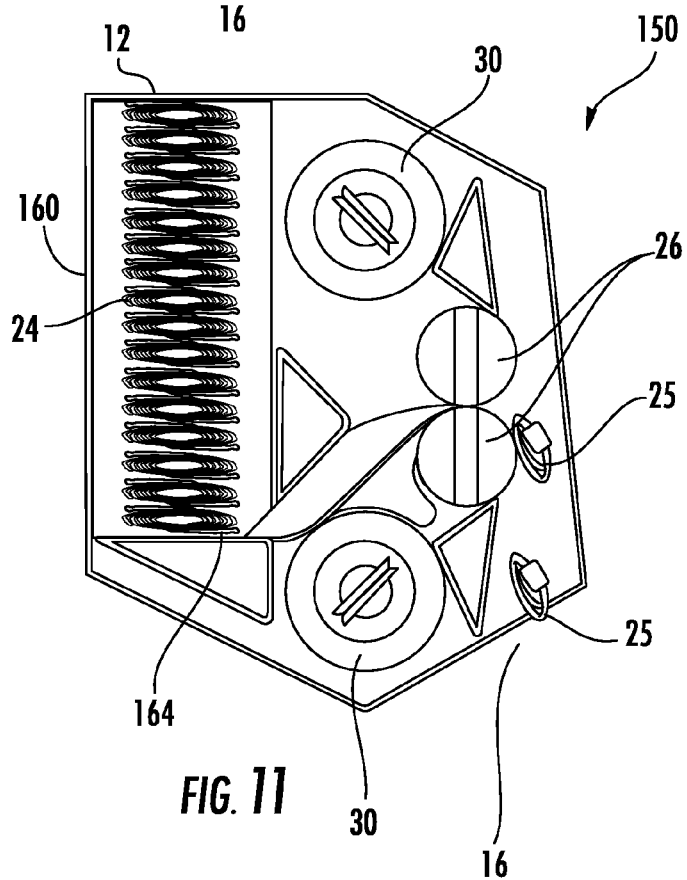

FIG. 11 shows the dispenser 150 where the cartridge 160 does not include the slanted base 162. Instead, the cartridge 160 includes a square base 164 which is a lower portion of the cartridge 160 and is generally parallel to the horizontal.

The cartridge 160 of the dispenser 150 may be removable so that when all of the package strip 24 is used, the empty cartridge 160 may be easily removed and replaced with a filled cartridge 160. Alternatively, the cartridge 160 may be fixed within the dispenser 150 and simply refilled with additional package strip 24 when empty. In either configuration, the dispenser 150 stores the used packaging strip 24 for later disposal and recycling.

Figure 12:
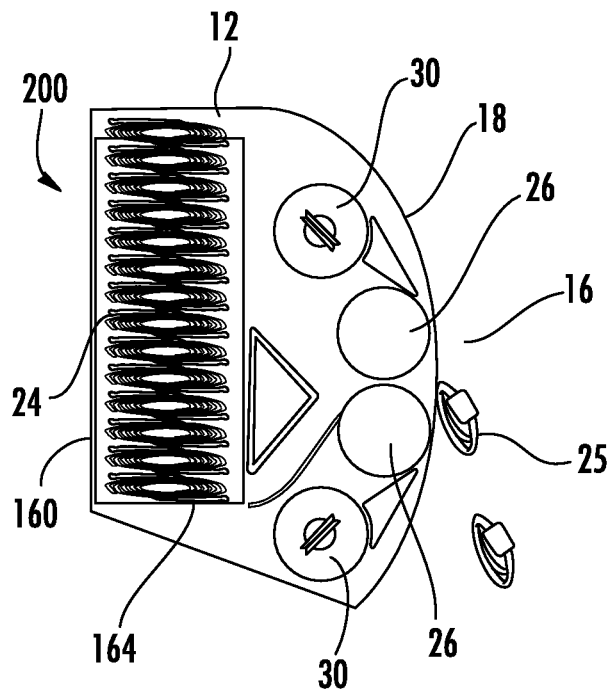
FIGS. 12 and 13 are front views of the dispenser in another embodiment.
Figure 13:
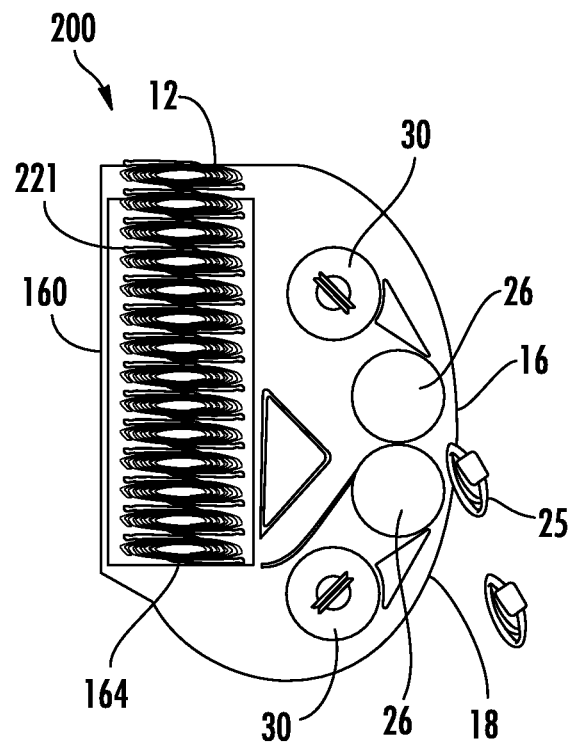

FIGS. 12 and 13 illustrate a dispenser 200 which is similar in many ways to the dispenser 150 of FIG. 11. That is, the dispenser 200 includes the cartridge 160 with the square base 164, the rollers 26, the waste spools, 30, etc. However, the dispenser 200 includes the dispensing portion 16 disposed on a front thereof That is, the dispensing portion 16 is not at a lower portion of the dispenser body 12 as previously discussed. Instead, the dispensing portion 16 is centrally disposed on the front cover 18 of the dispenser 200. This results in the earplug pairs 25 being ejected directly from the front casing of the dispenser 200, as shown. This allows for the overall volume of the dispenser 200 to be reduced. The dispensers 150 and 200 may further include the recycling receptacle discussed above which is configured to receive and retain the dispensed safety protection devices after being worn and to preserve the used devices for recycling.

Figure 14:
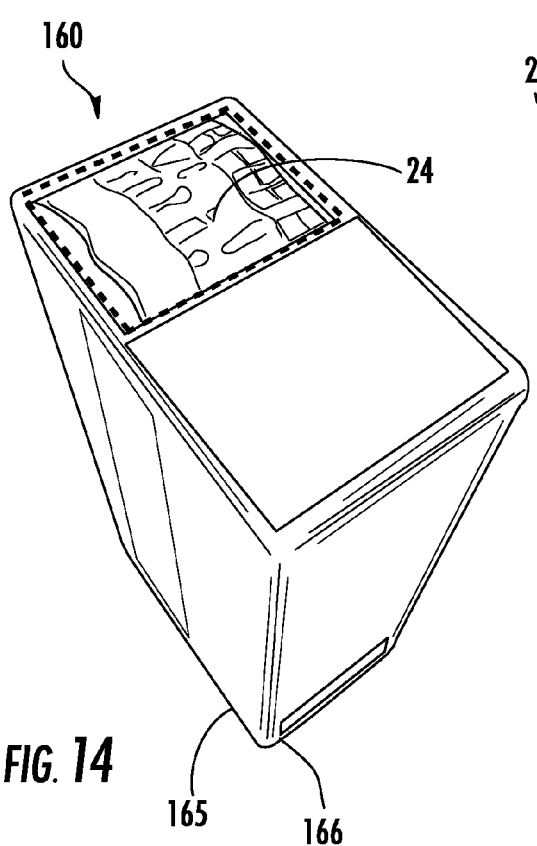
FIGS. 14-16 are various views of a cartridge to be used with the dispenser.
Figure 15:
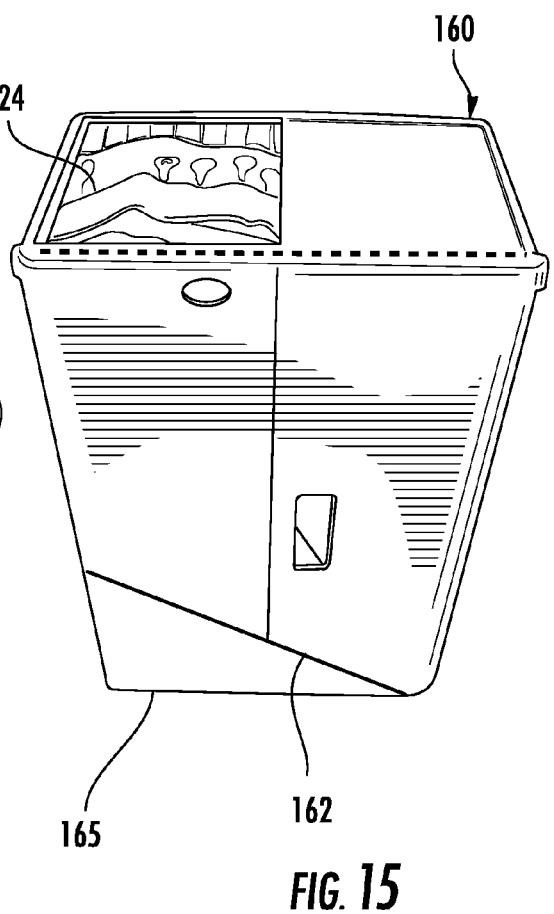
Figure 16:
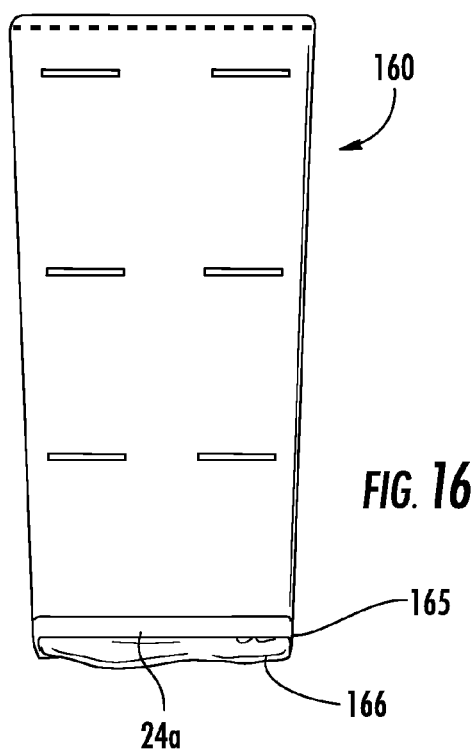

FIGS. 14-16 show various views of a cartridge 160 which is compatible with the dispensers 150 and 200. Here, the cartridge is removable and includes the slanted base 162. The cartridge 160 has a generally three-dimensional rectangular shape. That is, an external base 165 is square. However, in this embodiment, the slanted base 162 is disposed within the cartridge 160 as indicated in the drawing. The cartridge 160 includes a slot 166 through which the leading edge of the packaging 24' and 24" passes when the cartridge 160 is disposed in a dispenser and the package strip is accessed by user.

Figure 17:
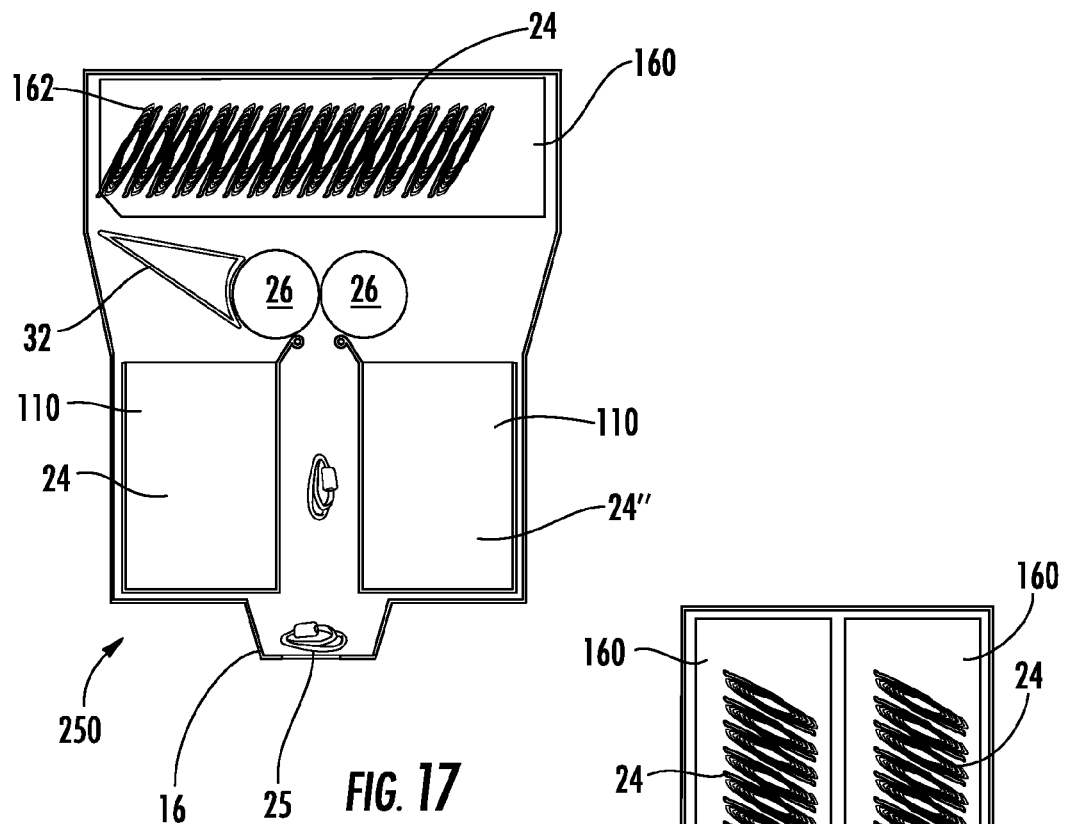
FIGS. 17 and 18 are front views of the dispenser in another embodiment

FIG. 17 shows a dispenser 250 including the rollers 26 and waste bins 110 previously discussed with respect to the dispenser 100 and the cartridge 160 of the dispenser 150. Here, the cartridge 160 is arranged in horizontal fashion above the rollers 26. The waste bins 110 are disposed adjacent one another and beneath the rollers 26. A user rotates the actuator 20 which turns the rollers 26 toward each other to thus pull the hearing protection device package strip 24 from the cartridge 160. The package strip 24 is ruptured at the rollers 26 as discussed thus freeing the earplug pairs 25 disposed therein. The spent packaging 24' and 24" is then deposited in the waste bins 110 as previously discussed for later recycling. Again, this dispenser 250 may include provisions and configurations, i.e., a receptacle or hopper, for receiving and retaining used safety protection devices for later recycling.

Figure 18:
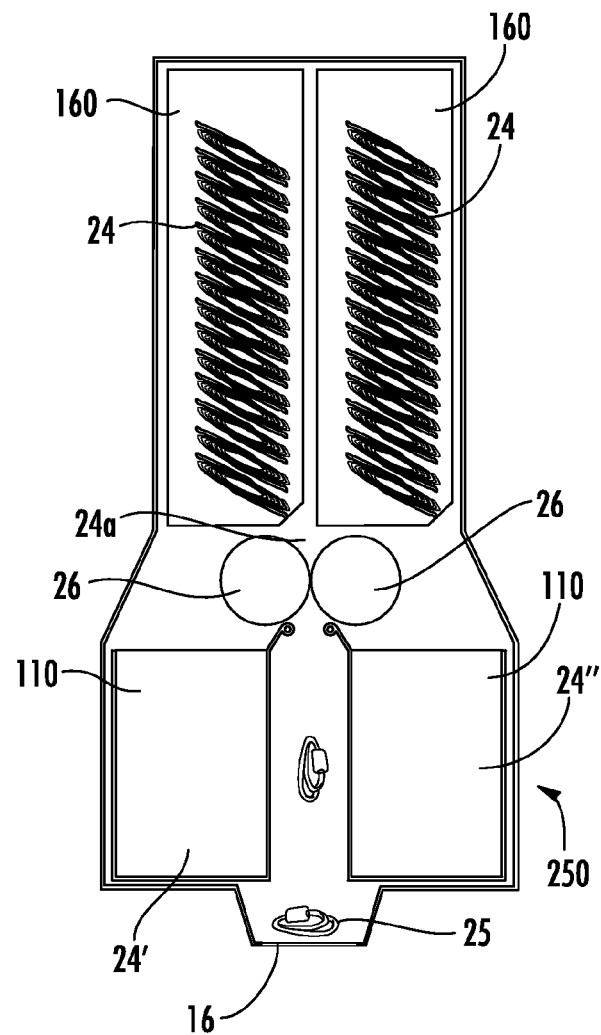

The dispenser 250 as shown in FIG. 18 includes two cartridges 160 disposed within the dispenser body 12 in a vertical configuration. The leading edge 24a of one of the package strips 24 from one of the cartridges 160 is engaged with the rollers such that rotation of the actuator 20 pulls the strip 24 between the rollers 26, thus rupturing the package 24 and releasing the earplug pairs 25. The spent package strip 24' and 24" is deposited in the waste bins 110. The second cartridge 160 is disposed with the dispenser 250 as a spare. Thus, when the first cartridge empties of all of the packaging 24, it is removed and discarded and the spare cartridge 160 is moved into place (if needed) and the leading edge 24a of its package strip 24 is engaged with the rollers. A new spare cartridge 160 may then be inserted to replace the removed cartridge. In this way, earplugs 25 may be dispensed essentially continuously.

The packaging strip 24 has thus far been described herein by way of example as comprising an elongated plastic sleeve. This sleeve is essentially composed of two strips of a plastic material bonded together at longitudinal edges thereof to form an elongated plastic envelope of sorts. As described, the strip 24 includes a plurality of sealing areas 23 extending transversely across the strip 24 to thus form the individual package pouches 23'. Alternatively, the packaging strip 24 may be composed of a single strip of plastic material having a first longitudinal edge and a second longitudinal edge. This strip may be longitudinally folded upon itself such that the first and second edges are brought into alignment. These edges may be sealed to one another to form the elongated envelope. Then, the sealing portions 23 may be applied to complete this embodiment of the package strip 24. Of course, the packaging strip 24 is not limited to being composed of a plastic material. For example, the strip 24 may be formed of a paper material or a paper or plastic composite material. Such paper or composite material would include perforation P similar to that described above in order to facilitate separation and opening of the packaging strip. The perforation P comprises any feature provided to the packaging strip 24 which facilitates opening thereof and/or discharge of the contents therefrom. For example, this scoring may include perforations, adhesive sealing, partial adhesive sealing, etc.

In other embodiments of the invention, the packaging strip 24 may be opened in any of a variety of ways in order to release the products disposed therein. For example, the strip 24 may include adhesive sealing at one or both longitudinal edges. The sealed strip portions may simply be pulled apart at the adhesive bond by action of the rollers to thus expose and dispense the stored products. Alternatively, the packaging strip 24 may include a plurality of the previously described perforations P. For example, the packaging strip 24 may include two parallel perforations P extending adjacent to on another longitudinally along a central portion of the strip 24. The parallel perforations P facilitate rupture of the packaging strip 24 by allowing separation of the strip 24 along one or both of the perforations P. Furthermore, the dual perforations P encourage continuous longitudinal separation of the strip 24 and prevent against errant transverse tearing of the strip 24. For example, a strip 24 used in the dispenser 10 will normally separate longitudinally along one of the parallel perforations P. Sometimes, the separating perforation P will evolve into a tear of the material forming the packaging strip 24 and thus diverge from the perforation P. This can occur, for example, where a thinner grade plastic is used to form the strip 24. If the errant tear migrates into the space between the parallel perforations P, the tear will quickly realign with the opposite perforation P, thus directing separation of the strip in a longitudinal direction. This prevents against a transverse or semi-transverse separation which could otherwise extend to a peripheral edge of the strip 24 and thus interfere with release of the packaged safety protection devices. Of course, the strip 24 may include any number of a plurality of generally parallel perforations, for example, two longitudinally extending perforations, three, four, etc. The perforations may be non-parallel. For example, two or more extending perforations may intersect at one or several locations. In alternate embodiments, the perforation(s) P may be non-centrally located on the packaging strip 24. For example, the perforation(s) P may be disposed proximate to a peripheral edge of the strip 24. In other embodiments, a scoring may be used in addition to or in place of the perforation P. The scoring comprises a portion of the packaging strip 24 which is partially severed such that when opposing forces are applied to the strip 24, it readily separates into multiple portions. For example, the scoring may comprise a longitudinal line cut into the material of the strip 24 and extending longitudinal along the strip 24 at a central region. The line is cut into, but not entirely though, the material forming the strip 24 and as such encourages separation as described above.

The width and length of the packaging strip 24 may of course be varied as necessitated by the shape and configuration of the packaged product. The sealing 23 may be applied in regular or irregular intervals, as desired. The spacing of adjacent sealing portions 23 may be varied to create different size pouches 23' dependent upon the particular requirements of the packaged products.

As described in detail, the dispenser of the invention is configured to be utilized with any of a plurality of products including safety protection devices. The safety protection devices have been described herein by example to include hearing protection devices, particularly earplugs. Advantageously, the dispenser may accommodate any type of earplug including: a roll-down foam earplug, such as for example the "E-A-R Classic" earplug produced by Aearo Company; a push-in foam earplug, such as for example the "Push-ins" earplug produced by Aearo Company; and a pre-molded reusable earplug, such as for example the "E-A-R Ultrafit" earplug produced by Aearo Company; and any combination or modification thereof. Further, the hearing protection device may comprise a semi-aural banded protector such as the "CABOFLEX" produced by Aearo Company or an earmuff such as product know as "E-A-R Muffs" also produced Aearo Company. The safety protection devices may further include safety eyewear such as safety glasses and/or goggles and/or head, face, and hand safety devices such as facepieces, face shields, respirators, gloves, etc.

The dispensers discussed herein may be configured to be mounted or otherwise hung or suspended on a wall or ceiling. Alternatively, the dispensers may be stand-alone units which are disposed in a free-standing manner on, for example, a tabletop.

The dispensers discussed herein have been described as manually operated arrangements. Particularly, it has been described that manual rotation of the actuator rotates and drives internal parts of the dispenser to thus cause dispensing of the hearing protection devices. It is noted that this rotatable actuator is only presented by way of example. The manual dispensement of hearing protection devices may be actuated by a lever, button, pull-knob, cord, etc. Additionally and/or alternatively, the dispenser may include a motor or the like and be electronically driven. Such arrangement may include a button, lever, switch, knob, motion sensor, etc., which a user actuates to initiate automatic electronic operation of the dispenser.

While the dispensers discussed herein are described as storing and dispensing hearing protection devices, particularly earplugs, the dispensers may be alternatively used for storing and dispensing any packaged consumer or industrial products such as, for example, eyewear, gloves or other handgear, office related items (such as packaged paper clips, binder clips), medical items, etc.

Dimensions and materials identified in this description and the attached Figures are for illustration purposes only and may vary depending upon the intended application in accordance with the teachings of the present invention. The present invention is not intended to be limited to the specific features of the Figures even though the invention encompasses the same.

Furthermore, it will be apparent to those skilled in the art that, while exemplary embodiments have been shown and described, various modifications and variations can be made to the present apparatus and method disclosed herein without departing from the spirit or scope of the invention. Accordingly, it is to be understood that the various embodiments have been described by way of illustration and not limitation.

The invention claimed is:

1. A universal dispenser arrangement, comprising:
   an elongated strip of packaged safety protection devices disposed at an interior of the dispenser;
   a drive arrangement configured to advance and rupture the strip of packaged safety protection devices and to release the safety protection devices therefrom upon demand of a user; and
   a waste arrangement configured to receive and retain the strip of packaging after said release of the safety protection devices;
   wherein the strip of packaged safety protection devices includes one or more strips of material, and each strip of material includes a perforation which extends generally along a longitudinal length of the strip, wherein the perforation facilitates the rupture of each strip of material.

2. The dispenser arrangement of claim 1, wherein the strip of packaged safety protection devices is wound about a spool disposed at the interior.

3. The dispenser arrangement of claim 1, wherein the strip of packaged safety protection devices is made of plastic.

4. The dispenser arrangement of claim 1, wherein the strip of packaged safety protection devices further comprises sealed areas extending across a width of the strip at intervals along the longitudinal length to delimit individual package pouches for containing individual safety protection devices.

5. The dispenser arrangement of claim 4, wherein the safety protection devices comprise one or more earplugs disposed in the package pouches.

6. The dispenser arrangement of claim 5, wherein the earplugs comprise one or more of a roll-down foam earplug, a push-in foam earplug, and a pre-molded reusable earplug.

7. The dispenser arrangement of claim 5, wherein the safety protection devices each comprise a pair of earplugs connected together by a cord.

8. The dispenser arrangement of claim 5, wherein the safety protection devices comprise one or more of a banded semi-aural device, an earmuff assembly, and a individual earmuff cup.

9. The dispenser arrangement of claim 4, wherein the safety protection devices comprise one or more of a safety eyewear device, a respirator device, a face shield, a safety glove, and a fall protection device.

10. The dispenser arrangement of claim 4, further comprising a guide configured to position the safety protection device centrally within the respective package pouch prior to said rupture.

11. The dispenser arrangement of claim 1, wherein the drive arrangement comprises a pair of adjacent drive rollers disposed at the interior of the dispenser, wherein the drive rollers are configured for axial rotation and are engaged with one another such that rotation of a first drive roller correspondingly rotates a second drive roller.

12. The dispenser arrangement of claim 11, further comprising an actuator disposed to be actuated by the user and configured to rotate the drive rollers.

13. The dispenser arrangement of claim 11, wherein the waste arrangement comprises a pair of waste rollers, each disposed in engagement with one of the drive rollers such that rotation of drive rollers correspondingly rotates the waste rollers.

14. The dispenser arrangement of claim 13, wherein strip of packaged safety protection devices extends between the drive rollers where the strip is separated longitudinally into a first strip portion which extends to and is engaged with a first of the waste rollers and a second strip portion which extends to and is engaged with a second of the waste rollers.

15. The dispenser arrangement of claim 1, wherein the waste arrangement comprises a pair of waste bins, wherein the strip of packaged safety protection devices extends between drive rollers where the strip is separated longitudinally into a first strip portion which extends into a first of the waste bins and a second strip portion which extends into the waste bins.

16. The dispenser arrangement of claim 1, wherein the strip of packaged safety protection devices is disposed within a cartridge at the interior of the dispenser wherein the cartridge is releasably retained at the interior so as to be selectively removable.

17. The dispenser arrangement of claim 16, wherein the strip of packaged safety protection devices include sealed portions across a width thereof at regular intervals along a length thereof, wherein the strip is disposed within the cartridge folded alternately at each sealed portion to form a "z" folded configuration.

18. The dispenser arrangement of claim 16, wherein the cartridge includes a lower interior surface which extends at an angle relative to a horizontal and an opening at the lower interior surface through which passes the strip of packaged safety protection devices.

19. The dispenser arrangement of claim 1, wherein the strip of packaged safety protection devices is disposed within a first cartridge removably disposed at the interior of the dispenser and wherein a spare strip of packaged safety protection devices is disposed within a second cartridge removably disposed at the interior generally adjacent to the first cartridge.

20. A method of dispensing safety protection devices, comprising:
    disposing said safety protection devices at intervals within an elongated package strip that includes one or more strips of material;
    perforating each of the one or more strips of material of the package strip along a longitudinal length of the elongated package strip;
    storing the package strip within a dispenser;
    advancing the package strip from the storage;
    rupturing the package strip along the perforation of each of the one or more strips of material to release the intervally disposed safety protection devices from the interior of the package strip; and
    collecting the package strip for disposal and recycling after said releasing of the safety protection devices.

21. The method of claim 20, wherein said storing comprises winding the package strip around a spool within the dispenser.

22. The method claim 21, wherein said storing comprises folding the package strip alternately at each interval within a cartridge disposable at the interior of the dispenser.

23. The method of claim 21, wherein said disposing safety protection devices comprises disposing one or more of a roll-down foam earplug, a push-in foam earplug, and a pre-molded reusable earplug.

24. The method of claim 21, wherein said disposing safety protection devices comprises disposing a pair of earplugs connected together by a cord.

25. The method of claim 21, wherein said disposing safety protection devices comprises disposing one or more of a banded semi-aural device, an earmuff assembly, and a individual earmuff cup.

26. The method of claim 21, wherein said disposing safety protection devices comprises disposing one or more of a safety eyewear device, a respirator device, a face shield, a safety glove, and a fall protection device.

27. The method of claim 21, further comprising sealing the package strip at intervals along its length to create package pouches in the strip to contain the intervally disposed safety protection devices.

28. The method of claim 27, further comprising positioning safety protection devices centrally within the respective package pouch prior to said rupturing.

* * * * *